United States Patent
Kangasniemi

[11] Patent Number: 6,116,901
[45] Date of Patent: Sep. 12, 2000

[54] DEVICE FOR USE PARTICULARLY IN THE REINFORCEMENT OF TEETH OR DENTAL PROSTHETIC DEVICE

[75] Inventor: Ilkka Kangasniemi, Turku, Finland

[73] Assignee: Stick Tech Oy, Turku, Finland

[21] Appl. No.: 09/212,268

[22] Filed: Dec. 16, 1998

[30] Foreign Application Priority Data

Jul. 12, 1998 [FI] Finland .................................. 982632

[51] Int. Cl.[7] ................................................ A61C 5/04
[52] U.S. Cl. .............................................. 433/89; 433/141
[58] Field of Search .................................. 433/89, 90, 80, 433/141

[56] References Cited

U.S. PATENT DOCUMENTS

| | | | |
|---|---|---|---|
| 2,930,061 | 3/1960 | O'Neil | 15/131.05 |
| 3,841,537 | 10/1974 | Marg et al. | 222/541 |
| 3,879,141 | 4/1975 | Shulman | 401/265 |
| 4,380,425 | 4/1983 | Edelman | 401/265 |
| 4,682,950 | 7/1987 | Dragan | 433/90 |
| 5,102,332 | 4/1992 | Uthoff | 433/6 |
| 5,244,388 | 9/1993 | Frush | 433/90 |
| 5,301,843 | 4/1994 | Groene et al. | 222/192 |
| 5,588,560 | 12/1996 | Benedict et al. | 222/106 |
| 5,693,033 | 12/1997 | Nita | 604/264 |

FOREIGN PATENT DOCUMENTS 0 292 026 11/1988 European Pat. Off. .

*Primary Examiner*—John J. Wilson
*Attorney, Agent, or Firm*—James C. Lydon

[57] ABSTRACT

A device for use particularly in reinforcement of teeth or dental prosthetic devices, where the device is used for wetting and for application of a reinforcing fiber bundle. The device includes a flexible pipe through the first end of which the reinforcing fiber bundle can be inserted and through the second end of which the reinforcing fiber bundle can be removed, where the wall of the pipe is treated so as to be essentially opaque to light intended for the curing of the reinforced fiber bundle, and a nozzle arranged at the second end of the pipe, the cross-section of the nozzle being smaller than the cross-section of the pipe.

12 Claims, 1 Drawing Sheet

DEVICE FOR USE PARTICULARLY IN THE REINFORCEMENT OF TEETH OR DENTAL PROSTHETIC DEVICE

BACKGROUND OF THE INVENTION

This invention relates to a device as defined in claim 1, said device being intended for use particularly in the reinforcement of teeth or dental prosthetic devices.

Fiber products are generally used in dentistry for splinting and reinforcing of teeth and for reinforcing of various dental prosthetic devices such as crowns, fixed bridges, removable dentures and so called surface attachable bridges or light or maryland type bridges. Such fiber reinforcement products either solely consist of fibers, or they are fiber reinforcement products preimpregnated with a polymer or a monomer. Commercially available products of this kind are listed in the following table 1.

TABLE 1

| Type of fiber | Product (brand) | Preimpregnation |
| --- | --- | --- |
| UHMWP[x) | Ribbond, DVA Fibers Connect, Fibre-Bind | none |
| | Fibrespan | monomer |
| Aramide | Kevlar | none |
| Glass | GlassSpan, Fiber Splint | none |
| | Vectris, FibreKor | monomer |
| | Stick, Stick Net | polymer |

[x)UHMWP = ultra high molecular weight polyethylene

In the UHMWP products, there is no attachment between the fibers and the polymer, the impregnation of the fibers is poor and the products result in an increase of fatigue strength of only about 25%.

In aramide fiber products the fibers do not either attach very well to the polymer and the impregnation of the fibers is poor.

In glass fiber products without preimpregnation by a polymer matrix, the impregnation of the fibers is poor and their strengths are poor.

The preimpregnated glass fiber products are expensive, but they result in a good strength. The international patent publication WO 96/25911 discloses such a porous prepreg based on glass fibers, wherein said prepreg is preimpregnated with a polymer.

The commercially available fiber reinforcement products are usually in woven form or in the form of a fiber bundle where the fibers are unidirectional. The handling of woven fiber products is rather easy. When such products are cut e.g. with scissors, the fiber bundles are fairly well kept together and they do not fray remarkably. The handling of non woven fiber bundles of unidirectional fibers is remarkably more difficult. When these products are cut, the individual fibers are not kept together by anything, and the fiber bundle may freely fall apart. This problem has been attempted to solve by tying the bundle together with an additional thread, by weaving the bundle or by preimpregnating the bundle with a porous polymer matrix. These solutions imply new problems. If the bundle is tied together with a thread or is woven, the fibers stay tightly together. This complicates the impregnation of the fiber bundle because the monomer liquid cannot easily penetrate in between the individual fibers. Another problem is that if the bundle is tightly tied or woven together, the fibers of the fiber bundle cannot be spread any longer. Fiber bundles impregnated with a polymer are easy to cut and they impregnate well with the monomer because of the existing polymer matrix between the fibers. Once impregnated with the monomer, the polymer matrix begins to dissolve into the monomer and the individual fibers begin to loosen from the bundle. As a result, the fiber bundle is difficult to handle on the mould or in the mouth because the fiber bundle is no longer well bound together. Secondly, a problem common to all types of glass fiber bundles is that the high tensile modulus of glass fibers forces the bundle to straigthen up. Therefore it is very difficult to apply the bundle onto curvy tooth arches.

In summary, the aim is that the fibers either can be kept together or spread, if desired. Furthermore, it is desirable that the fiber bundle can be formed to follow the shape of the tooth arch closely while keeping the control of the fibre bundle continuously. In addition, it is desirable that the wetting of the fiber bundle and the handling and storage thereof is safe because of the repeated skin contamination and the allergenic properties of the evaporating monomer. Moreover, it is desirable that the wetted fiber bundle, which at a later stage is cured with light (blue light), is not cured by room light or by the curing light from the light curing apparatus before the wetted fiber bundle is applied on the intended place.

SUMMARY OF THE INVENTION

The above object is achieved by a device in accordance with the invention, which is characterized by what is disclosed in the characterizing part of the appended claims.

Thus, the object of the invention is a device for use particularly in reinforcement of teeth or dental prosthetic devices, wherein said device is used for wetting and for application of a reinforcing fiber bundle (for example, on a tooth or a dental prosthetic device). The device is characterized in that it comprises a flexible pipe, through the first end of which the reinforcing fiber bundle can be inserted and through the second end of which the reinforcing fiber bundle can be removed, wherein the wall of the pipe is treated so as to not essentially pass the light intended for the curing of the reinforcing fiber bundle, and a nozzle arranged at the second end of the pipe, the cross-section of the nozzle being smaller than the cross-section of the pipe.

BRIEF DESCRIPTION OF THE DRAWINGS

The invention is described in more detail by refering to the attached drawings where.

DETAILED DESCRIPTION OF THE PREFERRED EMBODIMENTS

Figure 1:
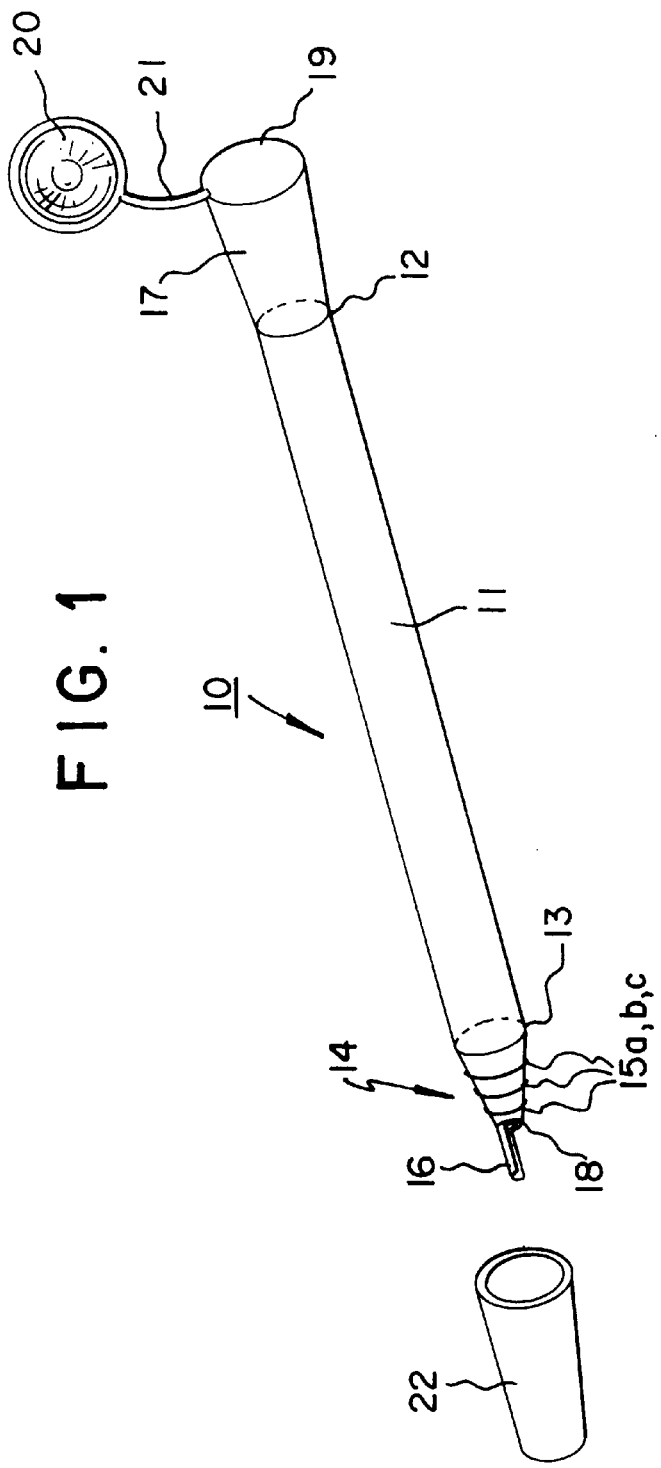
FIG. 1 shows the device according to the invention according to a preferred embodiment.

FIG. 1 shows the device 10 according to the invention in a preferred embodiment. The device comprises a pipe 11, made of a flexible material, through the first end 12 of which the reinforcing fiber bundle (not shown in the figure) can be inserted into the pipe. Through the second end 13 of the pipe the reinforcing fiber bundle is removed, i.e. applied onto its place. The lenght of the pipe preferably long enough to allow the longest reinforcing fiber bundle to be straight therein. In practice, such a longest reinforcing fiber bundle will correspond to the length of the tooth arch, i.e. about 15 cm. The cross-section of the pipe must be so large that at least one reinforcing fiber bundle and the liquid necessary for its wetting without difficulty fit into the pipe. According to a preferred embodiment, the cross-section of the pipe is large enough (i.e. the diameter is about 4 mm) to allow the pipe to contain several reinforcing fiber bundles simultaneously side by side, so that they can be wetted simultaneously. When the reinforcing fiber bundle (or bundles) is inserted into the pipe, the wetting liquid (monomer liquid) dissolving the polymer mass of the reinforcing fiber bundle, is added. The softened reinforcing fiber bundle is cured, for example, with blue light (wave length about 400 nm) after the reinforcing fiber bundle has been removed from the device 10 and applied onto its final place. Because the pipe is manufactured of a flexible material, suitably of plastic, which is inert in relation to the wetting liquid (i.e. the wetting liquid does not react with it, does not adhere to or penetrate it) the distribution of the wetting liquid to the reinforcing fiber bundle can be enhanced by pressing the wall of the pipe. It is essential that the wall of the pipe is treated so as to not essentially pass the light intended for the curing of the reinforcing fiber bundle. This can be suitably arranged by using orange coloured plastic, because the orange colour absorbs blue light. Alternatively, black colour could be used, but orange colour is preferred because it allows the pipe to be transparent. A nozzle 14 is arranged at the second end 13 of the pipe, wherein the cross-section of the nozzle is smaller than the cross-section of the pipe 11. Due to this feature, the reinforcing fiber bundle is kept well together when leaving the device. According to a preferred arrangement, the nozzle 14 is shaped as shown in FIG. 1, i.e. it is a conically shaped piece tapering in the running direction of the fibers. The diameter of the discharge outlet 18 of the nozzle 14 is preferably about 1.5 mm. The conically shaped nozzle 14 may be equipped with one or more cutting lines 15a, 15b, 15c . . . for fiber reinforcement bundles of various thicknesses. When thicker fiber bundles are used, the conically shaped nozzle can be cut at the desired point. The cutting lines 15a, 15b, 15c . . . can be marked with the inner diameter of the discharge outlet (e.g. 2, 2.5 and 3 mm) which helps the user to cut the nozzle at the appropriate point.

The nozzle is preferably manufactured of a stiff material. In the arrangement according to FIG. 1, the end 13 of the pipe in contact with the nozzle 14 may also be made of a stiffer material than the main part of the pipe.

The device is preferable equipped with a tip 16 made of a stiff material. This tip 16 may be connected to the pipe 11 itself, or, as shown in FIG. 1, connected to the nozzle 14. When part of the wetted fiber bundle is drawn (or pushed with a plunger) out of the nozzle 14 and applied on its final place, the reinforcing fiber bundle can be firmly pressed by the tip 16 against the tooth or dental prosthetic device for the time of curing. Thanks to the tip 16, it is not necessary to use other dental instruments in order to stick the reinforcing fiber bundle to its place.

Figure 2:
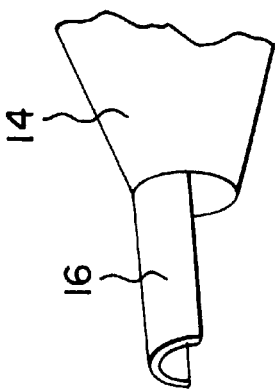
FIG. 2 shows the tip of the device according to FIG. 1.

FIG. 2 shows more closely a preferable embodiment of the tip 16. The tip is a bent piece, the form of which best corresponds to a certain segment of a pipe. The tip is placed so that its concave surface becomes directed against the reinforcing fiber bundle. The concave surface keeps the individual fibers of the reinforcing fiber bundle firmly together and prevents their fraying. The width of the tip is suitably about 1 mm.

Furthermore, the device is suitably provided with a feeding nozzle 17 connected to the first end 12 of the pipe. According to the embodiment shown in FIG. 1, the feeding nozzle is a conically shaped piece tapering in the running direction of the fibers. The diameter of inlet opening 19 of the feeding nozzle is preferable about 6 mm. The conical shape facilitates the inlet of the wetting liquid into the pipe.

Figure 3:
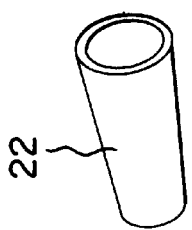
FIG. 3 shows a protecting cap for the nozzle of the device according to FIG. 1.

The feeding nozzle 17 according to FIG. 1 is provided with a cover 20, which via a strip 21 is connected to the device. FIG. 3 shows a separate protecting cap 22 used to protect the nozzle 14 and the tip 16.

The device can also comprise a plunger, going inside the pipe, with which the reinforcing fiber bundle can be pushed out from the device.

It shall be noted that it is not necessary that the cross-section of the pipe is circle-formed. Thus, it can for example be oval or otherwise different from a circle.

The device according to the invention can be used for application of any reinforcing fiber bundle onto the tooth or to the dental prosthetic device. The reinforcing fiber bundle can thus be impregnated or non-impregnated. The curing of the reinforcing fiber bundle can be carried out with light or chemically. The light curing is preferable because it enables selective curing of the part of the reinforcing fiber bundle removed from the device. The device is particularly useful for the application of a glass fiber based reinforcing fiber bundle.

The device can be used clinically for splinting of teeth, in the manufacture of orthodontic devices and in the manufacture of prosthetic bridges, both in the patient's mouth and in laboratory. In laboratory, the device can be used for the manufacture of many different kinds of prostheses.

Furthermore, the device can be used generally in the medical and surgical field, for example for reinforcement of different orthopedic prostheses by a reinforcing fiber bundle.

The above mentioned embodiments of the invention are only examples of the use of the inventive idea. It is apparent for the specialist in the field that the various embodiments of the invention may vary within the scope of the appended claims.

What is claimed is:

1. A device for use in the reinforcement of teeth or dental prosthetic devices, wherein said device is used for wetting and for application of a reinforcing fiber bundle on its place, characterized in that it comprises
    a flexible pipe which contains a reinforcing fiber bundle which is curable when exposed to a predetermined wavelength of light, and said pipe having an open first end through which said reinforcing fiber bundle is inserted and an open second end through which said reinforcing fiber bundle can be removed, wherein the wall of the pipe is opaque to light at least at the predetermined wavelength and
    a nozzle arranged at the second end of the pipe, the cross-section of the nozzle being smaller than the cross-section of the pipe.

2. The device according to claim 1, characterized in that the nozzle is a conically shaped piece tapering in the running direction of the fibers.

3. The device according to claim 2, characterized in that the conically shaped piece is equipped with one or more cutting lines for dispensing fiber reinforcement bundles of various thicknesses.

4. The device according to claim 1, characterized in that the nozzle is manufactured of a stiff material.

5. The device according to claim 1, characterized in that the device is equipped with a tip , arranged in connection with the nozzle or the pipe and manufactured of a stiff material.

6. The device according to claim 5, characterized in that the tip is a bent piece having its concave surface directed against the reinforcing fiber bundle.

7. The device according to claim 1, characterized in that to the first end of the pipe is attached a feeding nozzle.

8. The device according to claim 7, wherein said feeding nozzle is a conically shaped piece tapering in the running direction of the fibers.

9. The device according to claim 1, characterized in that it also comprises a plunger inside the pipe with which the reinforcing fiber bundle can be pushed out from the device.

10. The device according to claim 1, characterized in that the pipe is manufactured of a suitable plastic material which is inert in relation to a liquid for wetting the reinforcing fiber bundle.

11. The device according to claim 1, characterized in that the pipe is orange coloured.

12. The device according to claim 1, characterized in that the cross-section of the pipe is sufficiently large such that several reinforcing fiber bundles simultaneously located in the pipe side by side.

* * * * *